United States Patent [19]

Ishizawa et al.

[11] Patent Number: 4,970,468

[45] Date of Patent: Nov. 13, 1990

[54] ANALYTICAL EQUIPMENT WITH FUNCTION OF DETECTING LIQUID SURFACE CAPACITIVELY

[75] Inventors: Masato Ishizawa, Katsuta; Hiroshi Hashimoto, Naka, both of Japan

[73] Assignee: Hitachi, Ltd., Tokyo, Japan

[21] Appl. No.: 397,855

[22] Filed: Aug. 24, 1989

[30] Foreign Application Priority Data

Aug. 26, 1988 [JP] Japan ................. 63-210743

[51] Int. Cl.⁵ .............. G01R 27/26; G01N 35/02; B01L 3/02
[52] U.S. Cl. ................. 324/662; 324/686; 73/864.24; 422/67; 422/100; 422/106
[58] Field of Search ............ 324/71.1, 661, 662, 324/663, 671, 689, 686; 340/620; 73/864.24, 864.25, 304 C, 290 R; 422/106, 63, 67, 100

[56] References Cited

U.S. PATENT DOCUMENTS

| 3,635,094 | 1/1972 | Oberli .................. 73/864.24 |
| 4,228,831 | 10/1980 | Kerns ................. 422/100 X |
| 4,326,851 | 4/1982 | Bello et al. .......... 73/864.24 X |
| 4,736,638 | 4/1988 | Okawa et al. ........ 73/864.24 |
| 4,818,492 | 4/1989 | Shimizu ............. 73/864.24 X |
| 4,897,244 | 1/1990 | Wallace et al. ....... 73/864.24 X |

FOREIGN PATENT DOCUMENTS 57-82769 5/1982 Japan.
62-194464 8/1987 Japan.

*Primary Examiner*—Reinhard J. Eisenzopf
*Assistant Examiner*—Jack B. Harvey
*Attorney, Agent, or Firm*—Fay, Sharpe, Beall, Fagan, Minnich & McKee

[57] ABSTRACT

Analytical equipment, in which liquid substances in sample containers and reagent containers are delivered to reaction cells by a vertically movable probe. The sample containers and the reagent containers are supported on a rotatable metal plate. The metal plate is rotated to place one of the sample containers or reagent containers at a sample or reagent pipetting position. The probe transmits a high-frequency signal to detect a change in electrostatic capacitance between itself and the metal plate at a time the probe is put in contact with a liquid substance in the sample or reagent container. A spline shaft for moving the probe in a vertical direction has a detection plate, and a control signal is generated when the detection plate reaches a predetermined position. The generation of the high-frequency signal is stopped when the probe begins to make a descending motion until the control signal is generated, to reduce the adverse effect of disturbing waves on various parts.

8 Claims, 9 Drawing Sheets

OUTPUT OF OSCILLATION CIRCUIT 22

OUTPUT OF DIFFERENTIATION CIRCUIT 23

WHEN PROBE IS PLACED OVER REAGENT CONTAINER

WHEN PROBE IS PUT IN CONTACT WITH LIQUID SURFACE

OUTPUT VOLTAGE OF ELECTROSTATIC CAPACITANCE DETECTION CIRCUIT 25

WHEN PROBE IS PLACED OVER REAGENT CONTAINER

ANALYTICAL EQUIPMENT WITH FUNCTION OF DETECTING LIQUID SURFACE CAPACITIVELY

BACKGROUND OF THE INVENTION

The present invention relates to analytical equipment having a function of detecting a liquid surface, and more particularly to analytical equipment capable of detecting a liquid surface on the basis of a change in electrostatic capacitance at a time a probe is put in contact with the liquid surface.

An example of an automatic analyzer, in which a probe acting as a pipette has a function of detecting a liquid surface, is disclosed in JP-A-57-82769. In this example, a pipetting probe provided with a liquid-surface sensor falls toward a liquid surface in a reagent container, and the volume of a reagent remaining in the reagent container is calculated from the moving distance of the probe necessary for the probe to reach the surface of the reagent. In this example, however, a pair of electrodes (that is, a pipetting probe electrode and a liquid-surface detecting electrode) make a vertical motion, as one body. Accordingly, it is impossible to use the above probe in a case where a liquid container has a covering membrane for preventing the evaporation of a reagent or the like. In view of this fact, a liquid-surface sensor of the electrostatic capacitance type has been used in an automatic analyzer.

It is disclosed in U.S. Pat. No. 3,635,094 that after the surface of a liquid substance has been detected by utilizing electrostatic capacitance, a predetermined quantity of liquid substance is sucked by a probe. In this case, a liquid-surface detecting electrode is separated from the probe. In order to simplify such a structure, the probe itself has been used as a liquid-surface detecting electrode.

The latest example of an automatic analyzer provided with a liquid-surface sensor of the electrostatic capacitance type is disclosed in JP-A-62-194464. In this example, a probe which is formed by uniting a liquid-surface detecting electrode and a pipetting tube in one body, is inserted into a liquid container having a covering membrane, and the volume of a liquid substance remaining in the containers is calculated from the height of the container and the moving distance of the probe which is moved at a constant velocity.

In a case where the electrostatic capacitance between a probe which also serves as a liquid-surface sensor, as an electrode disposed under a liquid container is measured, there arises a problem that a high-frequency signal applied to the probe exerts an adverse effect on the operations of other members. The above-referred JP-A-194464 pays no attention to this problem.

Further, in a case where a liquid surface in a container which has a covering membrane for preventing the evaporation of a liquid substance, is detected by a pipetting probe serving also as a liquid-surface detecting electrode, when the probe is inserted into or withdrawn from the container, the probe is frequently put in contact with the covering membrane. For example, let us consider a case where a reagent container has the covering membrane. When the probe is withdrawn from the container, a liquid reagent on the other surface of the probe adheres to the covering membrane. In a case where the liquid reagent in the container is taken out only once, the liquid reagent adhering to the covering membrane offers no problem. In a case where the liquid reagent in the container is pipetted a plurality of times, however, there is a fear that a small amount of liquid reagent adhering to the covering membrane is erroneously detected as a liquid surface in the container. The above-referred JP-A-62-194464 pays no attention to this problem.

OBJECTS OF THE INVENTION

It is an object of the present invention to provide analytical equipment which can suppress the generation of a high-frequency signal at a time a liquid substance is delivered from a container to another container by a probe.

It is another object of the present invention to provide analytical equipment which can prevent a liquid substance which is attached to the covering means of a container, from being erroneously regarded as the liquid substance in the container.

It is a further object of the present invention to provide analytical equipment which has a function of detecting a liquid surface in a container in a simple manner independently of whether or not the container has a covering membrane.

SUMMARY OF THE INVENTION

According to the present invention, there is provided analytical equipment which comprises a probe for delivering a liquid substance in a container supported on a conductor to another container. A control signal is generated at a time the probe approaches the container supported on the conductor in the course of a descending motion. A high-frequency signal is generated for detecting a change in electrostatic capacitance between the probe and a metal plate in response to the control signal and the signal is no longer generated when the probe is put in contact with a liquid substance in the container supported on the conductor.

DESCRIPTION OF THE PREFERRED EMBODIMENTS

Figure 1:
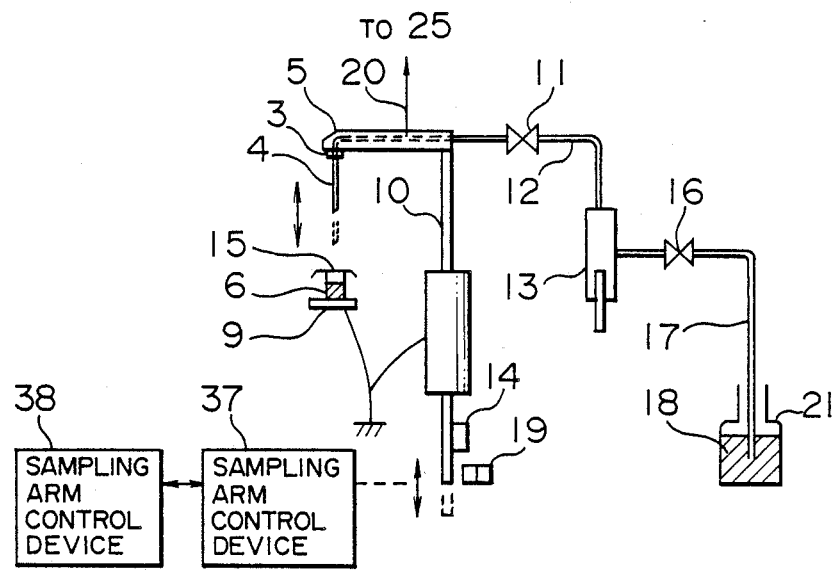
FIG. 1 is a schematic diagram showing a sampling mechanism which is used in an embodiment of analytical equipment according to the present invention.

Even in a case where a high-frequency signal is applied to a probe electrode which is supported by a device such as a rotatable arm, other members are scarcely affected by the high-frequency signal (that is, disturbing wave) during a period when the probe electrode is inserted into a container. In the present invention, attention is paid to a fact that a liquid surface to be detected lies under the upper end of a container, and a high-frequency signal is applied to a probe after the probe has reached a position which is spaced apart from the upper end of the container only a short distance in an upward direction, in the course of a descending motion, to reduce the adverse effect of the disturbing wave.

Further, in a case where the container has a covering membrane, a reference value control signal is generated before the probe reaches the covering membrane, and the value of electrostatic capacitance in a period when the probe having passed through the covering membrane falls toward a liquid surface in the container, is stored as a reference value. In a case where a liquid substance adheres to the covering membrane, the value of electrostatic capacitance varies greatly when the outer surface of the probe is put in contact with the covering membrane. However, the outer surface of the probe is kept in contact with the covering membrane during a period when the probe descends toward the surface of the liquid substance in the container. Accordingly, in this case, also, the value of electrostatic capacitance in the above period can be used as the reference value. The amount of liquid substance adhering to the covering membrane is less than the amount of liquid substance loaded in the container. Accordingly, it is possible to detect the difference between the reference value and the value of electrostatic capacitance at a time the probe reaches the surface of the liquid substance in the container.

In a preferred embodiment of analytical equipment according to the present invention, an electrode plate for mounting a plurality of liquid containers thereon is provided to be used as one electrode, a reagent container having a covering membrane and a sample container having no covering membrane are mounted on the electrode plate, and the surface of a liquid reagent in the reagent container and the surface of a liquid sample in the sample container are detected by the same probe, to deliver the liquid reagent and the liquid sample to a reaction cell.

In more detail, the preferred embodiment comprises a ground electrode for grounding a plurality of liquid containers, a metal probe electrode capable of being inserted into each of the containers, an electrostatic capacitance detector connected to the ground electrode and the probe electrode for generating a signal corresponding to the electrostatic capacitance between the ground electrode and the probe electrode, an output device for generating a reference value control signal, a storage device for storing the output of the electrostatic capacitance detector at a time a completion signal indicative of the termination of the reference value control signal is generated as a reference value, liquid level detector for comparing the reference value stored in the storage device with the output of the electrostatic capacitance detector to generate a liquid level detection signal when the output of the electrostatic capacitance detector exceeds the reference value, and an oscillation controller for controlling the generation of a disturbing wave during a period when a liquid level detecting operation is performed.

Now, explanation will be made of an embodiment of analytical equipment according to the present invention, with reference to FIGS. 1 to 14. FIG. 2 shows the external appearance of the present embodiment. Referring to FIG. 2, a disk 8 is rotated through a predetermined angle with the aid of well-known driving motor and a metal plate 9 is disposed under the whole of the bottom of the disk 8. The metal plate 9 is grounded, and serves as one electrode of a liquid level detecting device. A multiplicity of sample containers 7 are arranged in an inner part of the disk 8, and a plurality of reagent container 6 are arranged in an outer part of the disk 8 in accordance with analytical items. The sample container 7 which is to be loaded with a blood sample, is different in size from the reagent container 6 which is to be loaded with a liquid reagent for reaction. Hence, the metal plate 9 is formed stepwise so that the upper end of the sample container becomes equal in level to the upper end of the reagent container.

Figure 2:
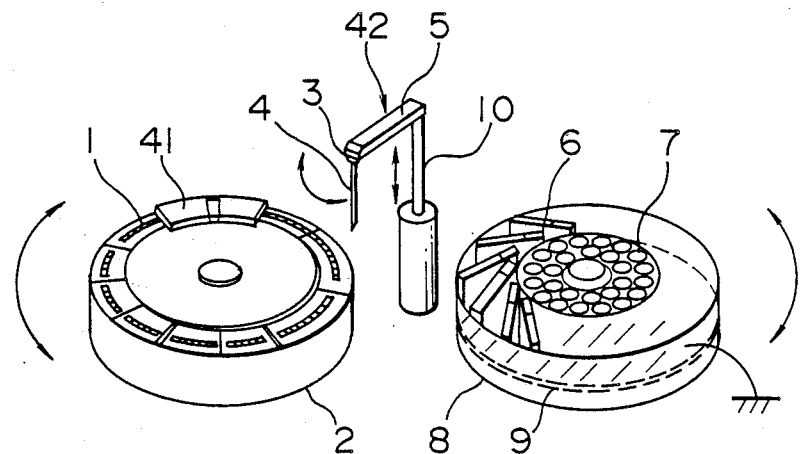
FIG. 2 is a schematic diagram showing the exterior of an embodiment of analytical equipment according to the present invention.

As shown in FIG. 1, a membrane 15 made of plastics is stretched on the upper end of the reagent container 6. In the present embodiment, the sample container 7 has no covering membrane. However, a covering membrane may be stretched on the upper end of the sample container 7. Referring back to FIG. 2, a multiplicity of cuvette (that is, reaction containers or reaction cells) 1 are arranged on a reaction disk 2 along the circumference thereof. Further, in the vicinity of the reaction cell train, there is provided a cleaning mechanism 41 for washing the reaction cells 1 and a fluorophotometer (not shown) for irradiating one of the reaction cells 1 with exciting light to measure the intensity of fluorescence emitted from a measured sample (that is, a blood sample having reacted with a reagent) in the reaction cell. The reaction disk, 2 is intermittently rotated by a well-known driving device.

The blood sample in the sample container 7 and the liquid reagent in the reagent container 6 are delivered to one reaction cell 1 on the reaction disk 2 by a sampling mechanism 42, when the sample container 7 and the reagent container 6 are placed at a predetermined sample intake position and a predetermined reagent intake position, respectively. The spline shaft 10 of the sampling mechanism 42 can make a vertical motion and a rotary motion, with the aid of a sampling-arm driving device 37. A pulse motor included in the driving device 37 receives a control signal from a sampling arm control device 38. An arm 5 is fixed to the spline shaft 10, and a probe electrode 4, formed using a metal pipe, is supported by the arm 5 through an insulator 3.

As shown in FIG. 1, the spline shaft 10 is provided with a detection plate 14. When the probe electrode 4 makes a descending motion, the detection plate 14 moves across a photo-interrupter 19 for a predetermined time to interrupt light. A reference value control signal is generated during a period when the detection plate 14 moves across the photo-interrupter 19. The probe electrode 4 is coupled with a tube 12 through a solenoid valve 11, and the tube 12 is coupled with a tube 17 through a syringe 13 and a solenoid valve 16. An end portion of the tube 17 is inserted into a vessel 21 which stores a chasing liquid (that is, pure water) 18. The metal probe electrode 4 is connected through a lead wire 20 to an electrostatic capacitance detection circuit 25, which will be explained later.

The probe electrode 4 acts as a pipette and one electrode of a liquid-surface sensor, and makes a vertical motion and a revolution round the shaft 10 in accordance with the operation of the sampling mechanism 42 so that a predetermined quantity of blood sample is sucked from the sample container 7 and then discharged in the reaction cell 1, and a predetermined quantity of liquid reagent is sucked from the reagent container 6 and then discharged in the reaction cell 1. The probe 4 detects a liquid surface in the sample container or reagent container, each time the probe 4 sucks the blood sample or liquid reagent from the sample container or reagent container.

Figure 3:
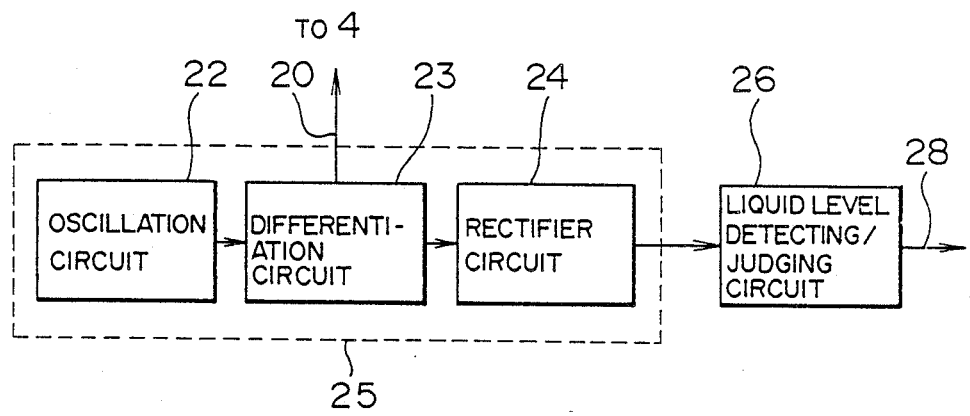
FIG. 3 is a block diagram showing the circuit configuration of a liquid-surface detecting device which is used in the embodiment of FIG. 2.

Next, a liquid-surface detecting operation will be explained. As shown in FIG. 3, the electrostatic capacitance detection circuit 25 is made up of an oscillation circuit 22, a differentiation circuit 23 and a rectifier circuit 24. The differentiation circuit 23 is connected to the metal probe electrode 4 through the lead wire 20, and the rectifier circuit 24 is connected to a liquid level detecting/judging circuit 26.

Figure 4:
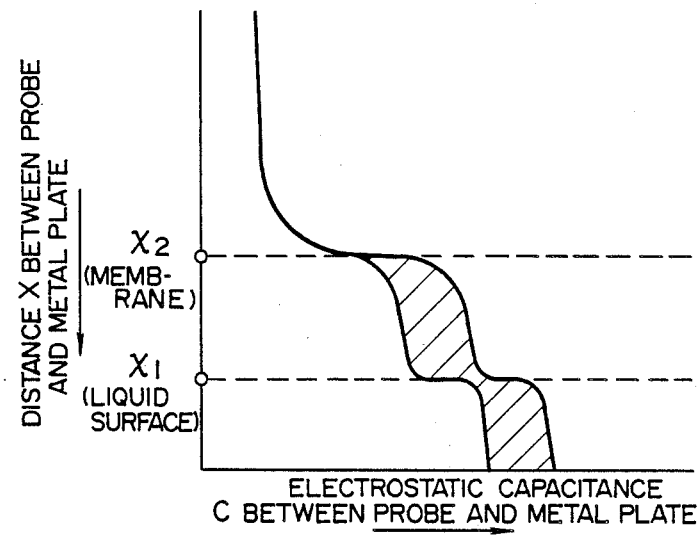
FIG. 4 is a graph for illustrating changes in electrostatic capacitance when the container has a covering membrane.
Figure 5:
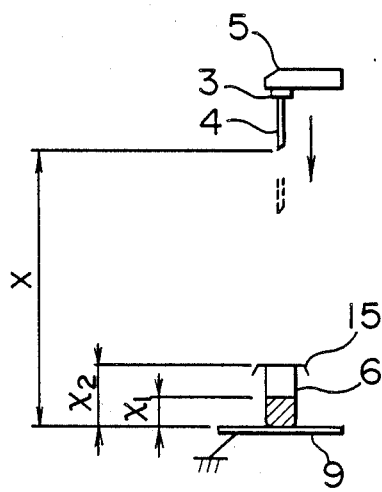
FIG. 5 is a schematic diagram for explaining the motion of a probe which produces the capacitance changes of FIG. 4.

First, explanation will be made of a liquid surface detecting operation for a case where a liquid container has a covering membrane, with reference to FIGS. 4 to 10. FIG. 4 shows the variation of the electrostatic capacitance between the probe electrode 4 and the metal plate 9 with the distance therebetween in a case where, as shown in FIG. 5, the upper end of the reagent container 6 is coated with the membrane 15 made of plastic. In other words, FIG. 5 shows the arrangement of the probe 4, the reagent container 6 and the metal plate 9 for obtaining the electrostatic capacitance versus distance characteristics of FIG. 4. Now, let us express the distance between the probe electrode 4 and the metal plate 9 at a time the probe electrode 4 is put in contact with the membrane 15 in the course of a descending motion, by $x_c$. Further, let us express the distance between the probe electrode 4 and the metal plate 9 when the probe electrode is put in contact with a liquid surface in the reagent container 6, by $x_1$. As shown in FIG. 4, the electrostatic capacitance C between the probe electrode 4 and the metal plate 9 changes at two positions indicated by the distance values $x_1$ and $x_2$. Further, in a case where a liquid substance adheres to the membrane 15, the electrostatic capacitance C at each of the positions indicated by the distance values $x_1$ and $x_2$ fluctuates as indicated by hatching. That is, the electrostatic capacitance at the position indicated by the distance value $x_1$ may vary so widely as to become nearly equal to the electrostatic capacitance at the position indicated by the distance value $x_2$. Hence, it is impossible to detect the liquid surface in such a manner that a predetermined electrostatic capacitance value is used as a reference value, and a measured electrostatic capacitance value exceeds the reference value when the probe electrode 4 reaches the liquid surface in the reagent container 6.

In the present embodiment, an electrostatic capacitance value at a time the probe electrode 4 is put in contact with the membrane 15, is used as a reference value, and a difference between an electrostatic capacitance value at a time the probe electrode 4 is put in contact with the liquid surface in the reagent container and the reference value is detected to make it possible to surely detect the liquid surface. For example, in a case where the reagent container 6 has 100 μl of pure water therein, the electrostatic capacitance value at a time the probe electrode 4 is put in contact with the liquid surface in the reagent container, is greater than the reference value by an amount corresponding to an increase of tens of millivolts in output voltage of the differentiation circuit 23.

Figures 6, 7A, 7B, 7C:
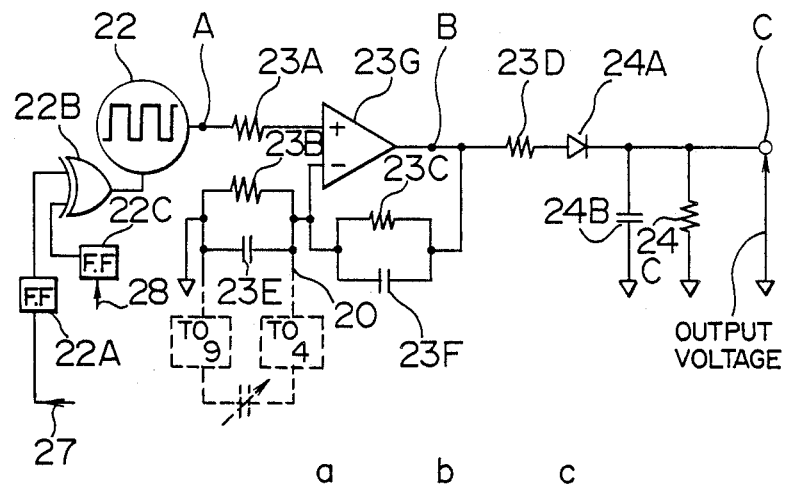
FIG. 6 is a circuit diagram showing an electrostatic capacitance detection circuit.
FIGS. 7A to 7C are waveform charts showing the signal waveforms at three points A, B and C of the electrostatic capacitance detection circuit of FIG. 6.

Next, the electrostatic capacitance detection circuit 25 will be explained. As shown in FIG. 6, the oscillation circuit 22 of the electrostatic capacitance detection circuit 25 supplies a pulse signal having a predetermined repetition period to the differentiation circuit 23. The oscillation circuit 22 is turned on or off in accordance with the output signal of an exclusive OR circuit 22B which is applied with a liquid level detection signal 28 and a reference value control signal 27 through flip-flop circuits 22A and 22C. The oscillation circuit 22 has an oscillation frequency of about 100 KHz. Hence, there is a fear that a disturbing wave is emitted from the probe electrode 4. In the present embodiment, the oscillation circuit 22 is turned on and off in the course of the descending motion of the probe electrode 4, to suppress the disturbing wave emitted from the probe electrode 4.

Next, the differentiation circuit 23 will be explained. The differentiation circuit 23 is made up of resistors 23A, 23B, 23C and 23D, capacitors 23E and 23F, and an operational amplifier 23G. The positive input terminal of the operational amplifier 23G is connected to the oscillation circuit 22 through the resistor 23A, and the negative input terminal of the operational amplifier 23G is connected to the probe electrode 4 through the lead wire 20. Further, a ground line is connected to the metal plate 9.

The differentiation circuit 23 differentiates the pulse signal from the oscillation circuit 22, in accordance with the electrostatic capacitance between the metal plate 9 and the metal probe electrode 4, and the differentiated signal thus obtained is applied to the rectifier circuit 24. In a period when the probe electrode 4 is not yet put in contact with a liquid reagent in the reagent container 6, an electrostatic capacitance of several femtofarads is produced between the metal plate 9 and the probe electrode 4 (where 1 femtofarad is equal to $10^{-15}$ farad). Accordingly, a waveform a shown in FIG. 7B is delivered from the differentiation circuit 23 to the rectifier circuit 24. The rectifier circuit 24 is made up of a diode 24A, a capacitor 24B, and a resistor 24C. When the rectifier circuit 24 is applied with the waveform a, the output signal of the rectifier circuit 24 has a level a shown in FIG. 7C. When the probe electrode 4 is put in contact with the membrane 15 which is stretched on the top of the reagent container 6, the electrostatic capacitance between the metal plate 9 and the probe electrode 4 is increased to hundreds of femtofarads, and thus the output voltage of the differentiation circuit 23 is increased by several millivolts. That is, the differentiation circuit 23 delivers a waveform b shown in FIG. 7B.

When the probe electrode 4 is put in contact with the liquid reagent in the reagent container 6, the electrostatic capacitance between the metal plate 9 and the probe electrode 4 is increased to several picofarads (where 1 picofarad is equal to $10^{-12}$ farad), and thus the output voltage of the differentiation circuit 23 is increased by tens of millivolts. That is, the differentiation circuit 23 delivers a waveform c shown in FIG. 7B. When the waveform b of FIG. 7B is applied to the rectifier circuit 24, the output signal of the rectifier circuit 24 has a level b shown in FIG. 7C. When the waveform c of FIG. 7B is applied to the rectifier circuit 24, the output signal of the rectifier circuit 24 has a level c shown in FIG. 7C. As mentioned above, the output signal of the rectifier circuit 24 has a signal level corresponding to the output voltage of the differentiation circuit 23.

Figure 8:
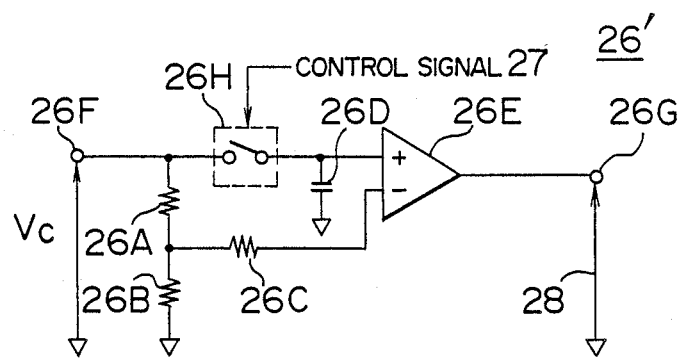
FIG. 8 is a circuit diagram showing a liquid level detecting/judging circuit which may be used when the case where a container has a covering membrane.
Figure 13:
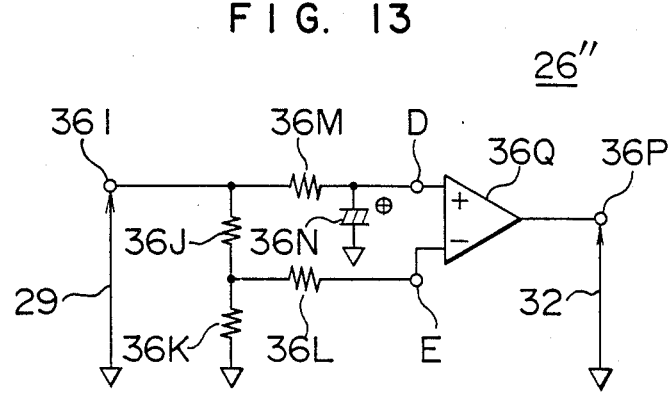
FIG. 13 is a circuit diagram showing a liquid level detecting/judging circuit which is used in a case where a container has no covering membrane.

The liquid level detecting/judging circuit 26, illustrated in FIG. 8, of FIG. 3 includes both a circuit 26' for the reagent container 6 having a covering membrane and a circuit 26", illustrated in FIG. 13, for the sample container 7 having no covering membrane, and one of the circuits 26' and 26" is selected in accordance with which of the reagent container 6 and the sample container 7 is placed at a corresponding one of the reagent intake position and the sample intake position.

The liquid level detecting/judging circuit 26' for the reagent container 6 having the covering membrane 15, as shown in FIG. 8, is made up of resistors 26A, 26B and 26C, a capacitor 26D, an analog switch 26H and a comparator 26E. Referring to FIG. 8, the output voltage $V_c$ of the electrostatic capacitance detection circuit 25 is applied to an input terminal 26F, and a liquid level detection signal 28 is delivered from an output terminal 26G. The analog switch 26H is turned on and off on the basis of the reference value control signal 27. Further, the capacitor 26D acts to set the reference value, and the comparator 26E acts as liquid-level detector.

The reference value control signal 27 is generated during a period when the tip of the probe electrode 4 descends from a position which is spaced apart from the covering membrane 15 of the reagent container 6 a distance of 3 to 5 mm in an upward direction, to a position which is spaced apart from the above membrane 15 a distance of 3 to 5 mm in a downward direction, and moreover is not yet put in contact with a liquid reagent in the reagent container 6.

Next, explanation will be made of an operation for detecting a liquid level in the reagent container 6.

Figure 9:
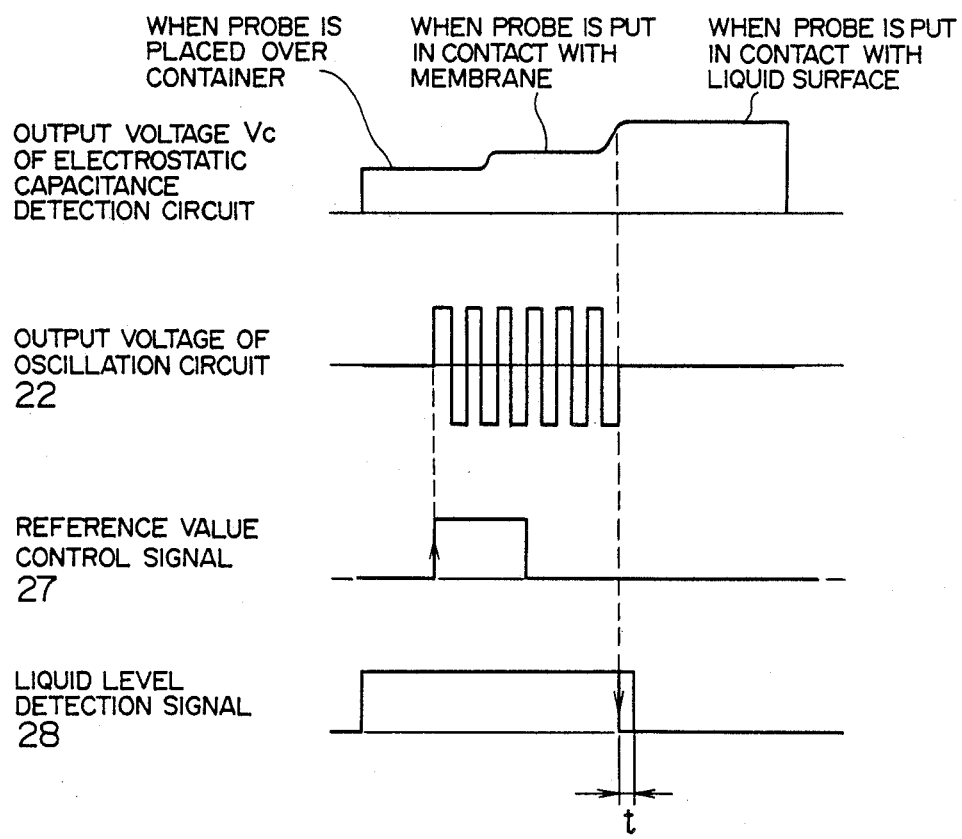
FIG. 9 is a waveform chart showing signal waveforms which are concerned with the circuit of FIG. 8.

When the probe 4 falls to a position which is spaced apart from the covering membrane 15 of the reagent container 6 a distance of 3 to 5 mm in the upward direction, the detection plate 14 begins to enter the photo-interrupter 19. Thus, the photointerrupter 19 begins to generate the reference value control signal 27. At this time, as shown in FIGS. 6 and 9, the leading edge of the reference value control signal 27 is detected by the flip-flop circuit 22C, and the oscillation circuit 22 begins to operate. Further, the analog switch 26H of FIG. 8 is closed, so that the capacitor 26D charges up to the output voltage $V_c$ of the electrostatic capacitance detection circuit 25. This output voltage $V_c$ is also applied to a voltage dividing circuit made up of resistors 26A and 26B, and the output voltage of the voltage dividing circuit is applied to the negative input terminal of the comparator 26E through the resistor 26C. It is to be noted that a ratio of the resistance value of the resistor 26A to the resistance value of the resistor 26B is selected so that the voltage applied to the negative input terminal of the comparator 26E is about 10 mV lower than the voltage of the capacitor 26D applied to the positive input terminal of the comparator 26E.

When the probe electrode 4 falls to a position which is spaced apart from the covering membrane 15 of the reagent container 6 a distance of 3 to 5 mm in a downward direction, the detection plate 14 passes through the photo-interrupter 19, that is, is outside the detection range of the photo-interrupter 19. Hence, the reference value control signal 27 is no longer generated, and the analog switch 26H opens. Thus, the output voltage of the electrostatic capacitance detection circuit 25 at this time is set, as a reference voltage, on the capacitor 26D. The reference voltage is held by the capacitor 26D for a predetermined discharge period thereof.

When the probe electrode 4 further falls so that the tip of the probe electrode 4 is put in contact with the liquid reagent in the reagent container 6, in the predetermined discharge period of the capacitor 26D, the output voltage $V_c$ of the electrostatic capacitance detection circuit 25 is increased by tens of millivolts, and thus the voltage of the negative input terminal of the comparator 26E becomes higher than the reference voltage held by the capacitor 26D. Hence, the liquid level detection signal 28 having a low level is generated, and the falling edge (that is, starting edge) of the liquid level detection signal 28 is detected by the flip-flop circuit 22A to stop the operation of the oscillation circuit 22.

If the descending motion of the probe 4 is stopped immediately after the probe 4 has been put in contact with the surface of the liquid reagent in the reagent container 6, the probe 4 will be unable to such a predetermined amount of liquid reagent from the reagent container 6. In the present embodiment, the liquid level detection signal 28 is delayed by a predetermined time t by the sampling arm control device 38, to continue the descending motion of the probe 4 so that the tip of the probe 4 reaches a position which is spaced from the surface of the liquid by a predetermined distance in the downward direction, thereby inserting the tip of the probe 4 into the liquid reagent sufficiently.

Further, the liquid level detecting/judging circuit 26' can perform a modified operation. That is, a change in output voltage of the electrostatic capacitance detection circuit 25, at a time the metal probe electrode 4 is put in contact with the covering membrane 15 of reagent container 6, can be detected by reversing the polarity of the control signal 27 applied to the analog switch 26H. In this case, the descending motion of the probe 4 is stopped at a time the probe 4 is put in contact with the covering membrane 15 of the reagent container 6.

Figure 10:
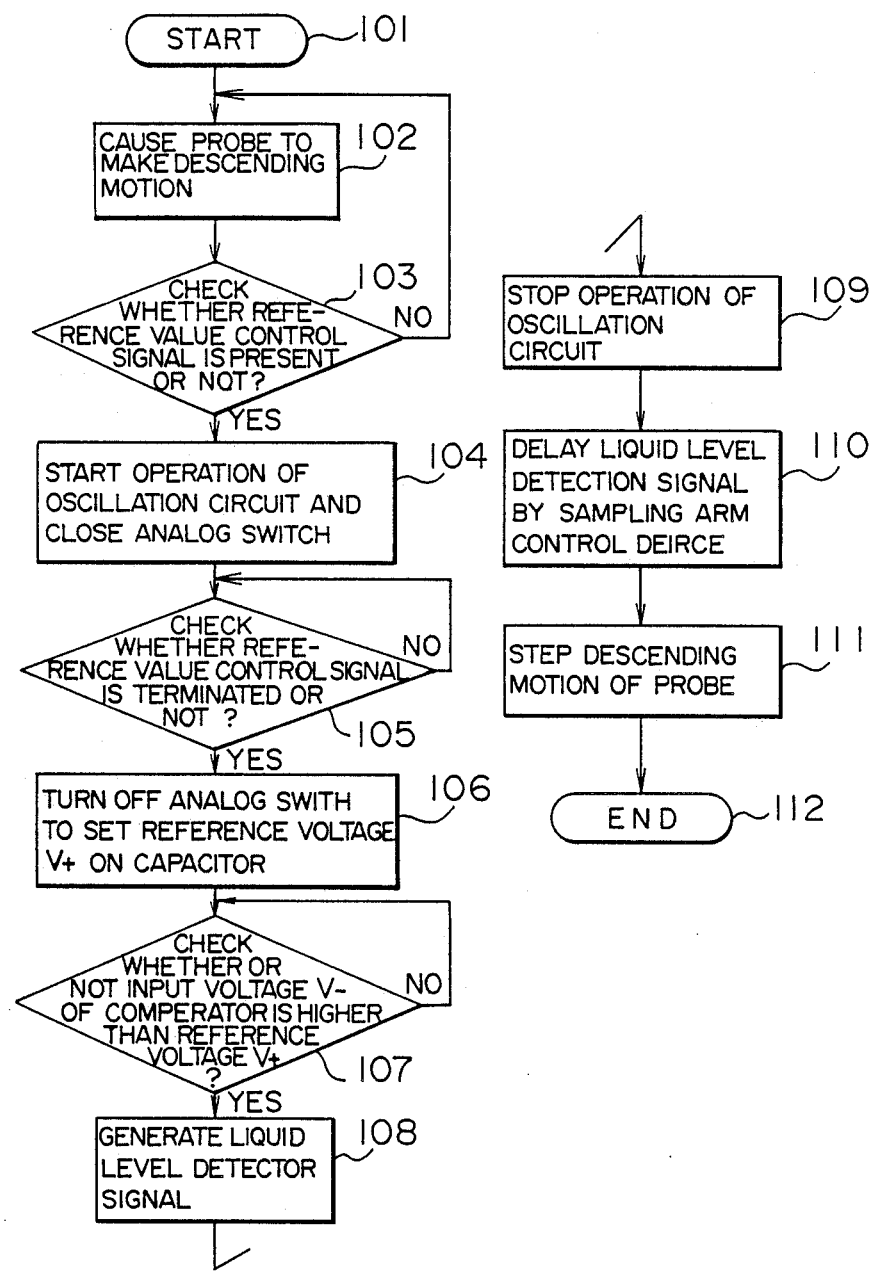
FIG. 10 is a flow chart showing the operation of the circuit of FIG. 8.

FIG. 10 is a flow chart showing a liquid level detecting operation which is performed when the liquid level detecting/judging circuit 26' of FIG. 8 is used. That is, the liquid level detecting operation from the "start" in step 101 to the "end" in step 112 is performed in the order of steps 102 to 111.

Next, explanation will be made of a liquid level detecting operation for the sample container 7 having no covering membrane. FIG. 13 shows a liquid level detecting/judging circuit 26" for a liquid container having no covering membrane. When the probe 4 is placed at the sample intake position where one of the sample containers exists, the circuit 26' of FIG. 8 is changed over to the circuit 26" of FIG. 13, in the liquid level detecting-/judging circuit 26 of FIG. 3.

Figure 11:
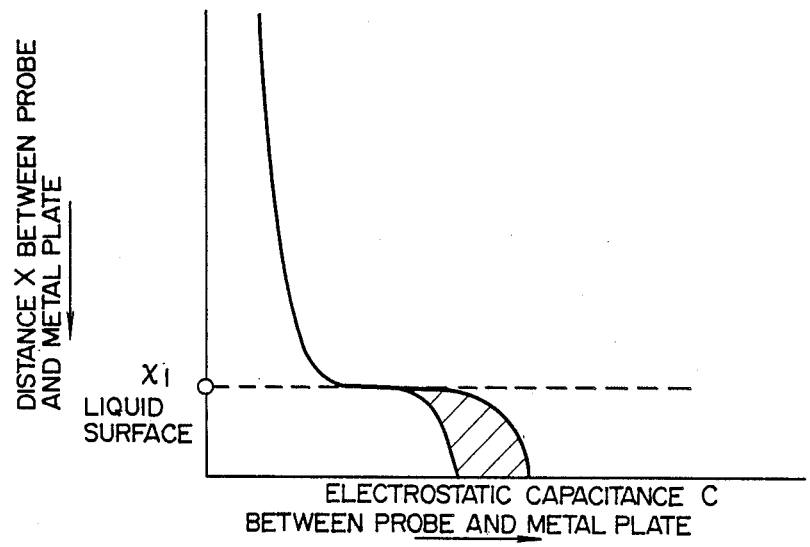
FIG. 11 is a graph for explaining a change in electrostatic capacitance in a case where the container has no covering membrane.
Figure 12:
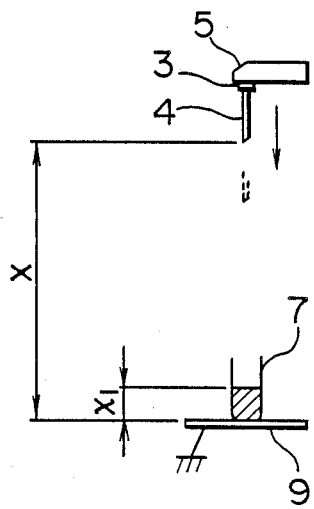
FIG. 12 is a schematic diagram for explaining the motion of a probe which produces the capacitance change of FIG. 11.

FIG. 12 shows the motion of the probe 4 in a case where a liquid level in the sample container 7 having no covering membrane is detected by the probe 4, and FIG. 11 shows the variation of the electrostatic capacitance C between the probe 4 and the metal plate 9 with the movement of the probe 4. Now, let us express the distance between the probe 4 and the metal plate 9 at a time the tip of the probe 4 is put in contact with a liquid surface in the sample container 7, by $x_1$. The electrostatic capacitance C changes abruptly only at the position of the probe 4 corresponding to the distance $x_1$. Hence, it is possible to detect the liquid surface in the sample container 7 by using the output voltage 29 of the electrostatic capacitance detection circuit at a time the tip of the probe 4 is put in contact with the liquid surface in the sample container 7, as a reference voltage (please refer to FIG. 14).

As shown in FIG. 13, the liquid level detecting/judging circuit 26" for the sample container 7 having no covering membrane, is made up of resistors 36J, 36K, 36L and 36M, a capacitor 36N, and a comparator 36Q. The output voltage 29 of the electrostatic capacitance detection circuit 25 is applied to an input terminal 36I, and a liquid level detection signal 32 is delivered from an output terminal 36P. When the probe 4 falls to a position which is spaced apart from the sample container 7 a distance of 3 to 5 mm in an upward direction, the photo-interrupter 19 detects the detection plate 14, and generates the reference value control signal 27, as in a case where the probe 4 falls toward the reagent container 6 having the covering membrane 15. The leading edge of the reference value control signal 27 is detected by the flip-flop circuit 22C, to operate the oscillation circuit 22. The output voltage 29 of the electrostatic capacitance detection circuit 25 is applied to the positive input terminal of the comparator 36Q through the resistor 36M and the capacitor 36N, and is also applied to a voltage dividing circuit formed of a series combination of the resistors 36J and 36K. The output voltage of the voltage dividing circuit is applied to the negative input terminal of the comparator 36Q. It is to be noted that a ratio of the resistance value of the resistor 36J to the resistance value of the resistor 36K is selected so as to make the voltage of the negative input terminal of the comparator 36Q about 10 mV lower than the voltage of the positive input terminal of the comparator 36Q.

Figure 14:
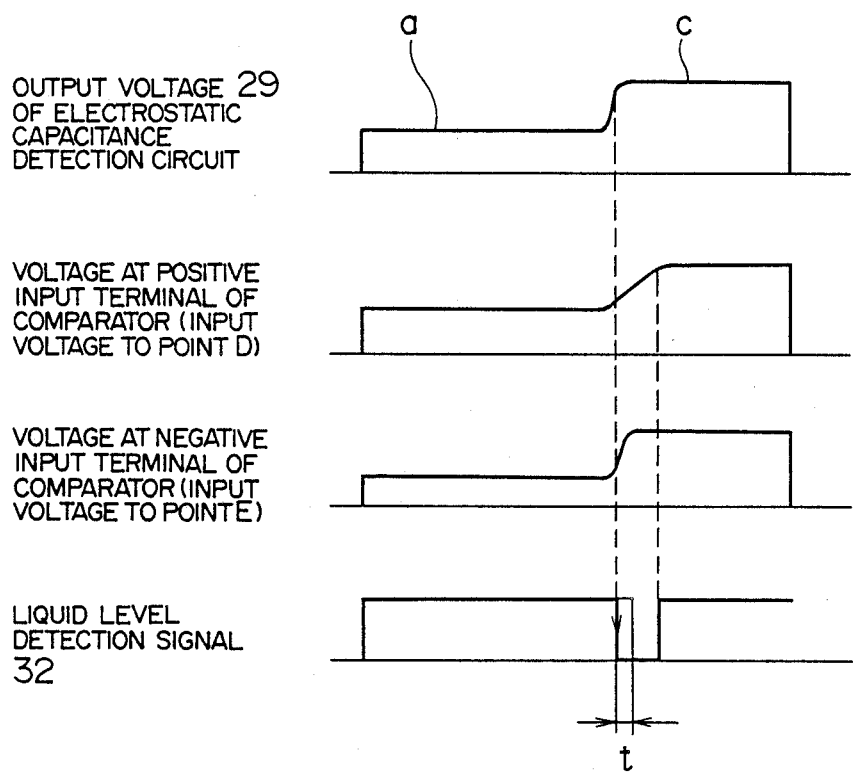
FIG. 14 is a waveform chart showing signal waveforms which are concerned with the circuit of FIG. 13.

When the probe 4 further falls so that the tip of the probe 4 is put in contact with a liquid surface in the sample container 7, the output voltage 29 of the electrostatic capacitance detection circuit 25 is increased by tens of millivolts. The positive input terminal of the comparator 36Q is connected to an input circuit made up of the resistor 36M and the capacitor 36N and having a time constant of about 0.1 sec. Accordingly, before the voltage of the positive input terminal of the comparator 36Q is increased by tens of millivolts, the voltage of the negative input terminal of the comparator 36Q is increased by tens of millivolts. Thus, the voltage of the negative input terminal can become higher than the voltage of the positive input terminal. At this time, a liquid level detection signal 32 having a low level is delivered from the output terminal 36P. The falling edge (namely, starting point) of the liquid level detection signal 32 is detected by the flip-flop circuit 22A to stop the operation of the oscillation circuit 22. As shown in FIG. 14, the liquid level detection signal 32 is delayed by a predetermined time t by the sampling arm control device 38 of FIG. 1. Thus, the descending motion of the probe 4 is stopped after the tip of the probe 4 has reached a position which is spaced apart from the liquid surface a predetermined short distance in a downward direction.

Figure 15:
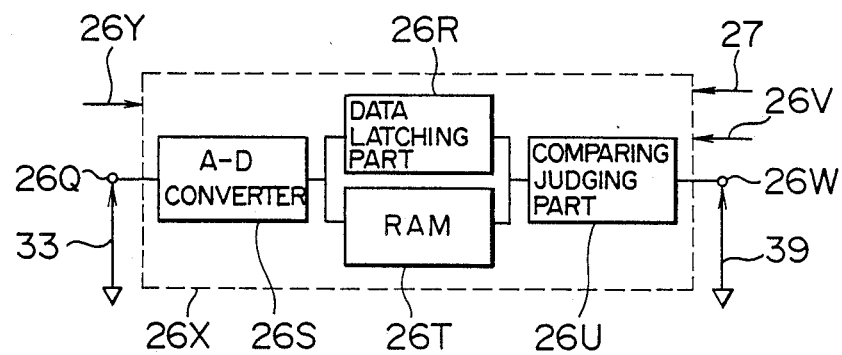
FIG. 15 is a block diagram showing a liquid level detecting/judging circuit which is used in another embodiment of analytical equipment according to the present invention.
Figure 16:
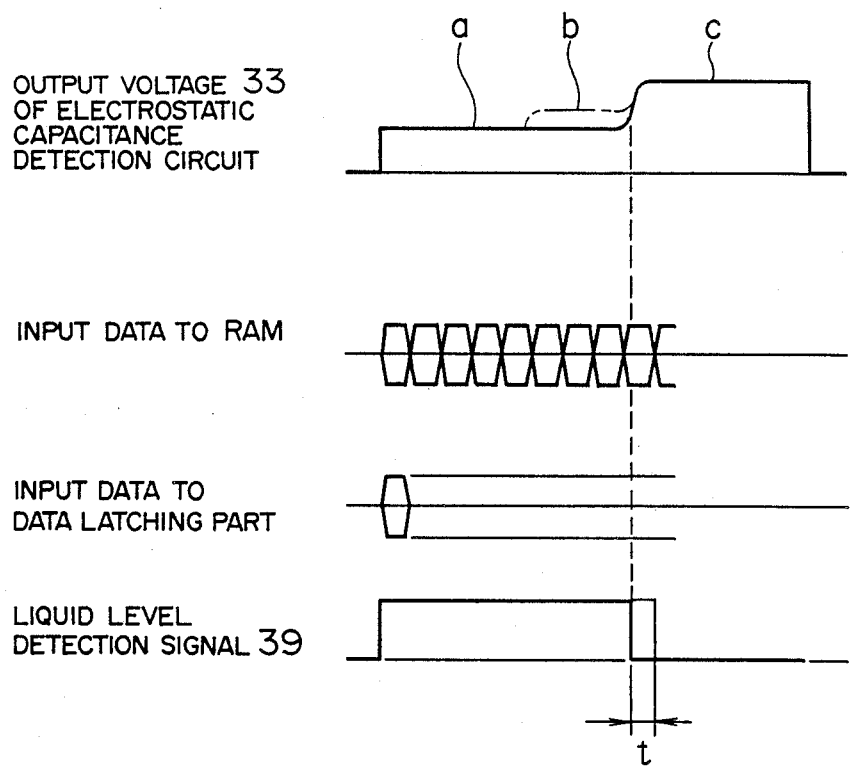
FIG. 16 is a waveform chart showing signal waveforms which are concerned with the circuit of FIG. 15.

Next, explanation will be made of another embodiment of analytical equipment according to the present invention, with reference to FIGS. 15 and 16. The present embodiment is different from the abovementioned embodiment, only in liquid level detecting/ judging circuit. The liquid level detecting/judging circuit included in the present embodiment can detect a liquid surface in a liquid container, independently of whether the liquid container has a covering membrane or not. This liquid level detecting/judging circuit, as shown in FIG. 15, is formed of a single-chip microcomputer 26X which includes an A-D converter 26S, a data latching part 26R, a random access memory (RAM) 26T, and a comparing/judging part 26U. The output voltage 33 of the electrostatic capacitance detection circuit 25 is applied to an input terminal 26Q, and a liquid level detection signal 39 is delivered from an output terminal 26W.

The comparing/judging part 26U detects a liquid surface in a liquid container from a change in characteristic of voltage 33 of the electrostatic capacitance detection circuit 25 in a case where the liquid container has a covering membrane and a change in characteristic of output voltage 33 of the electrostatic capacitance detection circuit 25 in a case where the liquid container has no covering membrane, in accordance with a program stored in the single-chip microcomputer 26X. It is judged by a selection signal 26Y applied to the single-chip microcomputer 26X whether or not the liquid container has a covering membrane.

Next, explanation will be made of an operation for detecting the liquid surface in the liquid container. The sampling arm driving device 37 causes the probe electrode 4 to make a vertical motion, and the vertical motion is controlled by the sampling arm control device 38.

When the probe electrode 4 makes a descending motion, the selection signal 26Y is applied to the single-chip microcomputer 26X, to indicate whether or not the liquid container has a covering membrane for preventing the evaporation of a liquid substance. The comparing/judging part 26U selects one of the above-mentioned change characteristics in accordance with the selection signal 26Y.

When the probe electrode 4 reaches a position which is spaced apart from the upper end of the liquid container a distance of 3 to 5 mm in an upward direction, the photo-interrupter 19 detects the detection plate 14, and generates the reference value control signal 27. The leading edge of the reference value control signal 27 is detected by the flip-flop circuit 22C, to operate the oscillation circuit 22. At the same time as the oscillation circuit 22 begins to operate, the output voltage 33 of the electrostatic capacitance detection circuit 25 is converted by the A-D converter 26S into a digital signal in synchronism with a clock signal 26V. The digital signal thus obtained is stored, as a reference value, in the data latching part 26R. Digital signals which are successively delivered from the A-D converter 26S in synchronism with the clock signal 26V, are stored in the RAM 26T.

First, let us consider a case where the upper end of the liquid container is covered with a membrane. When the probe electrode 4 descends so that the tip thereof is put in contact with the covering membrane, the output voltage 33 of the electrostatic capacitance detection circuit 25 is increased by tens of millivolts. When the probe electrode 4 penetrates the covering membrane and further descends so that the tip of the probe electrode 4 is put in contact with a liquid surface in the liquid container, the output voltage 33 of the electrostatic capacitance detection circuit 25 is further increased by tens of millivolts. On the basis of a program stored in the microcomputer 26X, the comparing judging part 26U detects only a change in output voltage of the electrostatic capacitance detection circuit 25 at a time the tip of the probe electrode 4 is put in contact with the liquid surface in the liquid container. DAta in the RAM 26T is successively compared with data in the data latching part 26R in synchronism with the clock signal 26V, to deliver the liquid level detection signal 39 having a low level, as shown in FIG. 16.

Next, let us consider a case where the liquid container has no covering membrane. In this case, the output voltage 33 of the electrostatic capacitance detection circuit 25 is increased by tens of millivolts, only when the probe electrode 4 descends so that the tip thereof is put in contact with the liquid surface in the liquid container. The comparing/judging part 26U detects a change in output voltage of the electrostatic capacitance detection circuit 25 at a time the tip of the probe electrode 4 is put in contact with the liquid surface in the liquid container, to deliver the liquid level detection signal 39. In the present embodiment, also, the liquid level detection signal 39 is delayed by a predetermined time t by the sampling arm control device 38. Thus, the descending motion of the probe electrode 4 is stopped after the tip thereof has been sufficiently inserted into a liquid substance in the liquid container.

We claim:

1. Analytical equipment comprising vertically-movable probe means for delivering a liquid substance in a liquid container supported on a conductor to another liquid container, high-frequency signal generating means for supplying a high-frequency signal to the probe means, and means for detecting a change in electrostatic capacitance at a time the probe is put in contact with the liquid substance in the liquid container supported on the conductor, the analytical equipment further comprising:
   means for generating a control signal at a time the probe means approaches the liquid container supported on the conductor in the course of a descending motion; and
   means for starting the operation of the highfrequency signal generating means on the basis of the control signal, and for stopping the operation of the high-frequency signal generating means on the basis of a signal produced when the probe means is put in contact with the liquid substance in the liquid container supported on the conductor.

2. Analytical equipment according to claim 1, wherein the control signal generating means includes a detection plate mounted on means which is used for moving the probe means, and a photo-interrupter disposed at a predetermined position.

3. Analytical equipment according to claim 1, wherein the control signal generating means produces a passage completion signal when a specified portion of the probe means has passed through a predetermined region in the course of a descending motion of the probe means.

4. Analytical equipment according to claim 3, wherein a range from a position which is spaced apart from the upper end of the liquid container supported on the conductor a predetermined distance in an upward direction, to a position which is spaced apart from the upper end of the liquid container supported on the conductor a predetermined distance in a downward direction, is the predetermined region for the tip of the probe means.

5. Analytical equipment according to claim 4, further comprising means for judging that a change in electrostatic capacitance at a time the probe means is put in contact with the liquid substance in the liquid container supported on the conductor indicates the arrival of the probe means at the surface of the liquid substance, and for judging that a change in electrostatic capacitance at a time the tip of the probe means exists in the predetermined region is caused by other factors than the surface of the liquid substance.

6. Analytical equipment according to claim 5, wherein covering means for preventing the evaporation of the liquid substance is provided at the upper end of the liquid container supported on the conductor, and the probe means penetrates the covering means in the course of a descending motion, to enter the inside of the liquid container.

7. Analytical equipment according to claim 1, wherein a plurality of first liquid containers, each provided with covering means for preventing the evaporation of a liquid substance, and a plurality of second liquid containers, each provided with no covering means, are supported on the conductor and wherein liquid substances in the first and second liquid containers are pipetted by the same probe means.

8. Analytical equipment according to claim 1, including a covering membrane provided at the upper end of the liquid container supported on the conductor, and wherein the detecting means detects the value of electrostatic capacitance at a time the tip of the probe membrane exists between the covering means and a liquid surface in the liquid container, and detects the value of electrostatic capacitance at a time the tip of the probe means is put in contact with the liquid substance in the liquid container.

* * * * *